United States Patent [19]

Orem et al.

[11] 4,069,220

[45] Jan. 17, 1978

[54] PROCESS FOR THE PRODUCTION OF PHENOLIC COMPLEXES OF HEXAMETHYLENETETRAMINE

[75] Inventors: Henry Philip Orem, Birmingham; David R. Hart, Auburn; Jerry E. Hill, Springville, all of Ala.

[73] Assignee: Jim Walter Resources, Inc., Birmingham, Ala.

[21] Appl. No.: 725,240

[22] Filed: Sept. 21, 1976

Related U.S. Application Data

[63] Continuation-in-part of Ser. No. 500,906, Aug. 27, 1974, abandoned.

[51] Int. Cl.$^2$ .................. C07D 295/02; C07D 295/08
[52] U.S. Cl. ...................................... 544/186; 544/185
[58] Field of Search ...................................... 260/248.5

[56] References Cited

U.S. PATENT DOCUMENTS

| 2,618,664 | 11/1952 | Hess et al. | 260/248.5 |
| 2,697,122 | 12/1954 | Hess et al. | 260/248.5 |
| 3,843,643 | 10/1974 | Ackerman et al. | 260/248.5 |

Primary Examiner—John M. Ford
Attorney, Agent, or Firm—James W. Grace

[57] ABSTRACT

A process has been developed for producing complexes of phenol or phenolic compounds and hexamethylenetetramine by mixing the ingredients with only enough water, or other suitable solvent, to promote the reaction. Heat liberated by the reaction is controlled by cooling the mixing chamber, and drying is accomplished by removing the small amount of solvent in conventional type dryers.

6 Claims, No Drawings

PROCESS FOR THE PRODUCTION OF PHENOLIC COMPLEXES OF HEXAMETHYLENETETRAMINE

This application is a continuation-in-part of pending application Ser. No. 500,906, filed on Aug. 27, 1974 of Henry Philip Orem, David R. Hart and Jerry E. Hill for Improved Process for the Production of Phenolic Complexes of Hexamethylenetetramine and the Reaction Products Thereof. Applicants claim the benefit of the earlier filing date of application Ser. No. 500,906, now abandoned.

BACKGROUND OF THE INVENTION

This invention relates to the field of preparing phenolic complexes of hexamethylenetetramine. When a water solution of hexamethylenetetramine and a water solution of phenol are combined, a white solid is precipitated. It may be filtered and dried to give a product known as phenotropin. Likewise, when a water solution of hexamethylenetetramine and a water solution of resorcinol are combined, a similar precipitate forms and may be filtered and dried to give a product known as resotropin. Other phenolic compounds may also be combined with hexamethylenetetramine to give similar products. Technical publications make reference to this type of preparation, both in water solution and other solvents such as alcohol. These products are useful in that they by themselves, or with other materials, when heated to higher temperatures, give resins that may be used to bind solids together. They are particularly useful in improving the adhesion of rubber to automobile tire cords, such as rayon, polyester, nylon, fiberglass and steel wire. An article, "The Structure of the Reaction Product of Resorcinol and Hexamethylenetetramine" by E. E. Potapov, I. A. Totorskii, I. D. Khodzhaeva and B. A. Dogadkin, published in SOVIET RUBBER TECHNOLOGY, Volume 24, No. 12, p. 19 (1965) - Translated by P. G. Williams, describes the product resotropin. In the article, "Formation of Resinous Structures in Rubbers During Vulcanization, and Their Effects of Reinforcement" by N. N. Burakova, V. G. Epstein, D. P. Babyuk (Yaroslav. Technol. Inst., Yaroslavl, USSR); Kolloid Zh. 32 (3), 337–41 (1970)(Russ), it is stated that the addition of resotropin with resorcinol-formaldehyde resin to synthetic rubber mixtures increased the mechanical strength and abrasion resistance and decreased the resilience of vulcanizates prepared from these mixtures.

It is also well known that resorcinol and hexamethylenetetramine have desirable effects on vulcanized rubber. There are, however, objections to this use of resorcinol and hexamethylenetetramine because each ingredient must be added to the masticating mixture at a separate and specific stage. Undesirable vapors and/or dust that may have deleterious health effects are liberated during incorporation of the resorcinol and hexamethylenetramine. However, this fuming and dusting is greatly reduced or eliminated when resotropin is used. Such use is therefore considered to be an improvement in the rubber manufacturing art. Other similar complexes herein described are also useful as rubber additives.

SUMMARY OF THE INVENTION

A solution containing phenol or resorcinol dissolved in a suitable solvent, such as water or alcohol, may be mixed with hexamethylenetetramine also dissolved in a suitable solvent. Upon such mixing, a product (phenotropin or resotropin, respectively) is precipitated, and subsequently filtered and dried. This procedure for preparing these products is well known in the art. However, part of the product remains dissolved in the filtrate; this filtrate may be recycled as solvent for a second, third and fourth batch. At about this stage, however, the filtrate must be discarded because of increasing concentrations of undesirable by-products, and new solvent is required. This leads to a loss of product remaining in the filtrate and loss of a valuable chemical when any solvent other than water is used. The wet filter cake must be dried, and special drying precautions would be required if a solvent other than water were used.

It has now been discovered that phenolic compounds will react with hexamethylenetetramine to form desired complex compounds, such as the phenotropin and resotropin discussed above, if the phenolic compound and hexamethylenetetramine are mechanically mixed, together with a small amount of water or other suitable solvent. This process may be best carried out utilizing mixing equipment, such as a dough mixer, pug mill, pony mixer, paddle mixer, ball mill, ribbon mixer or the like. The hexamethylenetetramine, the phenolic compound, and the water or other solvent are mixed together so as to control the heat liberated. The mixer may be externally cooled as required to prevent polymerization. Mixing is continued until reaction is complete; the product is then discharged and dried. The amount of solvent used is restricted such that no meaningful liquid phase coexists with the product. Therefore, solids-liquid separation, handling any disposal of filtrate, etc. are entirely eliminated by the present process. In order to facilitate introduction of one of the reactant materials, it may be convenient to combine that reactant with the solvent.

It has further been discovered that this process is not limited to reaction with phenol and resorcinol, but rather is a general process that can be used with many phenolic compounds. In addition, it has been found that the process is applicable where the phenolic compound has at least one position ortho to the hydroxyl group unsubstituted.

This invention presents a new and novel method of preparing the phenolic complexes of hexamethylenetetramine. The reaction is carried out in the presence of a minimum amount of solvent, and as a result, a considerable saving is realized in the energy required for drying the wet product, with a minimum loss of any expensive solvent that may be used. This process eliminates the unit operation of filtering a solid product from a slurry, and further eliminates the disposal of a filtrate that eventually would require further treatment to prevent contamination of a receiving stream. A further advantage of the process is that the yield of product is nearly quantitative, the only loss being mechanical loss in handling the material in process.

It is to be understood that this process is applicable to many compositions of matter, and although the examples describe batch operations for simplicity, the process is well suited for use in continuous operation, making manufacture of the product more efficient — entailing use of a minimum of labor and resulting in a greater uniformity of product quality.

This invention describes a process for preparing certain phenolic complexes of hexamethylenetetramine including certain new compositions of matter not described in previous scientific literature. A description of these materials and other advantages of the process are set forth hereinbelow.

DESCRIPTION OF THE PREFERRED EMBODIMENT

Applicants' preferred embodiment may be better understood from the following examples wherein all amounts are parts by weight.

EXAMPLE 1

A sigma-blade double-arm dough mixer (such mixers being well known to those familiar with the art) was charged with 848 parts of hexamethylenetetramine, and the mixer started. Then 632.6 parts of 90% phenol (10% water) were added over a period of fifteen minutes. The mixture was agitated for a period of 45 minutes; the temperature rose from 15° C to 21° C during the mixing period. The product was discharged from the mixer, and dried in an air dryer at 65° C for 19 hours. The dried product yielded 1,383.2 parts, representing a recovery of 97.6% of the materials, excluding water, charged to the mixer. This complex represents a ratio of 1 molecule of phenol to one of hexamethylenetetramine.

The small amount of heat liberated may be heat of reaction and/or heat of crystallization of the newly formed product. This heat, if sufficient, could cause rapid decomposition of the product, and thus, in some cases, it becomes necessary to cool the mixing chamber by water jackets, spray cooling the outside of the chamber, by circulating air through the mixer, or by other well-known means. This extraction of heat, directly or through the mixer wall or shell, does not alter the steps of the process, and only becomes necessary when the quantity of heat liberated is sufficient to be detrimental to the process. Applicants' experience with drying the materials described in the present invention shows that, as the materials initially react and are in a pasty soft stage, they are much more susceptible to decomposition at a given temperature than they are later when they become hard and crystalline in texture. In consideration of this characteristic, it is suggested that drying temperatures can be increased up to 110° C as the drying cycle progresses. However, initial drying temperatures should be held below 70° C.

EXAMPLE 2

A sigma-blade, double-arm dough mixer was charged with 1,242.4 parts of hexamethylenetetramine, and while mixing, 1,853.0 parts of 90% phenol (10% water) were added at a constant rate over a period of 35 minutes. The combined ingredients were mixed for an additional period of 30 minutes, discharged to an air dryer, and heated at 65° C for 17 hours. During the mixing, the temperature rose from 13° to 36° C. When the product was dried, it weighed 2,801.0 parts, representing a recovery of 96.3% of material charged to the mixer, excluding the water in the phenol. This product represents a complex containing 2 molecules of phenol to 1 molecule of hexamethylenetetramine.

EXAMPLE 3

A sigma-blade, double-arm dough mixer was charged with 900.0 parts of hexamethylenetetramine, and while mixing, 2,014.0 parts of 90% phenol (10% water) were added at a constant rate over a period of one hour. Mixing was continued for 40 minutes after the completion of the phenol addition. The temperature rose during the mixing from 17° C to 39° C. The product was discharged from the dough mixer, and placed in an air dryer at 65° C for 17 hours. The dried product gave 2,598.8 parts by weight, representing a yield of 95.8% recovery of the material charged to the mixer, excluding the water in the phenol. This product represents a complex containing 3 molecules of phenol to 1 molecule of hexamethylenetetramine.

EXAMPLE 4

A sigma-blade, double-arm dough mixer was charged with 981.3 parts of hexamethylenetetramine and 770.0 parts of resorcinol. The mixer was started, and after ten minutes, 122.6 parts of water were added uniformly over a period of 20 minutes. Mixing was continued for thirty minutes, and the temperature rose from 18° C to 23.5° C. The product was discharged from the dough mixer, and dried at 65°–70° C for 24 hours in an air dryer. 1,684.7 parts of resotropin were obtained, a recovery of 96.2% of the material charged to the dough mixer, excluding water.

EXAMPLE 5

A sigma-blade, double-arm dough mixer was charged with 1,121.5 parts of hexamethylenetetramine and 1,008.9 parts of pyrogallol. The mixer was started, and 213 parts of water were added uniformly over a period of 16 minutes. The material formed a thick pasty mass which became hard and broke up into a powder. During the mixing, the temperature increased from 15° to 34° C. The product was discharged from the mixer, and dried at 65°–70° C in an air dryer for about 14 hours. 2,052.5 parts of product was recovered, represeting 96.3% of the material charged to the dough mixer, excluding water.

EXAMPLE 6

A sigma-blade, double-arm dough mixer was charged with 981 parts of hexamethylenetetramine and 770 parts of resorcinol. The mixer was started, and after fifteen minutes, 122 parts of methyl ethyl ketone were added uniformly over a period of fifteen minutes. Mixing was continued for sixty minutes, and the temperature rose from 22° C to 34° C. The product was discharged from the dough mixer, and dried for 44 hours in an air dryer at 55° C. The product yield was 1,690 parts, representing a yield of 96.7% of the materials charged to the dough mixer, excluding methyl ethyl ketone.

EXAMPLE 7

A sigma-blade, double-arm dough mixer was charged with 1,000 parts of 4,4'-dihydroxydiphenyl sulfone and 560 parts of hexamethylenetetramine. The mixer was started and 156 parts of water were added over a period of four minutes. Mixing was continued for another 34 minutes during which the temperature rose from 28° C to 40° C. The product was discharged from the dough mixer and dried for 44 hours in an air oven at 55° C. A yield of 1,510 parts was obtained, representing a yield of 96.8% based on the ingredients charged to the dough mixer, excluding water.

EXAMPLE 8

A sigma-blade, double-arm dough mixer was charged with 841 parts of hexamethylenetetramine and 864 parts of B-naphthol. The mixer was started, and after four minutes a mixture containing fifty parts of water and fifty parts of iso-propyl alcohol was added uniformly over a period of four minutes. Mixing was continued for 92 minutes, and the temperature rose from 33° C to 38° C. The product was discharged from the dough mixer, and dried at 55° C for 44 hours in an air oven. The product yield was 1,705 parts, representing a yield of 100.0% of the materials charged to the dough mixer, excluding the water/iso-propyl alcohol solvent.

EXAMPLE 9

A sigma-blade, double-arm dough mixer was charged with 981 parts of hexamethylenetetramine and 770 parts of resorcinol. The mixer was started, and after five minutes, 122 parts of iso-propyl alcohol were added uniformly over a period of fifteen minutes. Mixing was continued for ninety minutes, and the temperature rose from 23° C to 34° C. The product was discharged from the dough mixer, and dried at 55° C for 44 hours in an air dryer. The product yield was 1,694 parts, representing a yield of 96.7% of the material charged to the dough mixer, excluding iso-propyl alcohol.

EXAMPLE 10

A sigma-blade, double-arm dough mixer was charged with 1,401 parts of hexamethylenetetramine. The mixer was started and 1,035 parts of 90% phenol (10% iso-propyl alcohol) were added uniformly over a 40-minute period. Mixing was continued for another 60 minutes and the product was discharged and dried 17 hours at 75° C in an air oven. During the mixing operation, the temperature of the batch rose from 30° C to 42° C. The yield of 2,147 parts indicated a recovery of 92.2% of the materials charged, excluding the solvent. This example represents the preparation of a complex containing one molecule of phenol to one molecule of hexamethylenetetramine in a non-aqueous solvent.

EXAMPLE 11

A sigma-blade, double-arm dough mixer was charged with 1,261 parts of hexamethylenetetramine. The mixer was started and 1,059 parts of 80% phenol (20% methyl ethyl ketone) were added uniformly over 40 minutes. Mixing was continued for another 60 minutes and the product was discharged and dried 17 hours at 75° C in an air oven. During the mixing operation, the temperature rose from 33° C to 41° C. This product representing a complex of one mole of phenol to one mole of hexamethylenetetramine in a second non-aqueous solvent yielded 1,903 parts or 90.3% of the charge, excluding the solvent.

EXAMPLE 12

A sigma-blade, double-arm dough mixer was charged with 1,175 parts of hexamethylenetetramine, and while mixing, 1,000 parts of 90% p-cresol (10% water) were added at a uniform rate over a period of 60 minutes. The combined ingredients were mixed for additional 60-minute period and the product was discharged into air dryer and dried for 24 hours at 75° C. During the mixing operation, the temperature rose from 30° to 41° C. The dried material weighed 1,871 parts, representing a recovery of 90.2% of the materials charged, excluding the water in the p-cresol solution.

EXAMPLE 13

A sigma-blade, double-arm dough mixer was charged with 855 parts of pulverized p-phenylphenol and 700.5 parts of pulverized hexamethylenetetramine. The mixer was started and 200 parts of water were added at a uniform rate over a 7-minute period. The charge was mixed for another 125 minutes and was discharged and dried at 75° C in an air oven for 17 hours. During the operation, the temperature rose from 29° C to 44° C. The product yield was 1,531 parts, representing a recovery of 98.4% of the charge, excluding water.

EXAMPLE 14

Seven batches of resotropin were made using selected percentages of water expressed as weight percentages of the total amount of solids charged. The general procedure was to charge a sigma-blade, double-arm dough mixer with 700 parts of hexamethylenetetramine and 550 parts of resorcinol, mix the solids for 10 minutes, uniformly add the intended amount of water over a 15-minute period, mix for another 60 minutes, discharge, and dry for 48 hours at 70° C in an air oven. The table indicates the levels of water used and the results.

| Percent Water | Product Yield | Product Appearance |
| --- | --- | --- |
| 0 | 94.7% | White Powder* |
| 5 | 98.3% | Light Flesh Powder |
| 10 | 97.2% | Light Flesh Powder |
| 20 | 99.2% | Flesh Powder |
| 30 | 101.3% | Dark Brown Lumps** |
| 40 | 98.1% | Dark Brown Lumps** |
| 50 | 96.8% | Dark Brown Lumps** |

*Tests indicate that no reaction occurred.
**Dark brown color indicates product decomposition has occurred.

The examples given herein show the process is successful with phenol, resorcinol, pyrogallol, dihydroxy diphenyl sulfone, B-naphthol, p-cresol and p-phenylphenol. In addition, o-tert-butylphenol, m-methoxyphenol, 3,5-xylenol, o-cresol, o-chlorophenol, o-pherylphenol, and 2,4-dichlorophenol have been found to be successful in this process.

The common thread for all these compounds is that they each have at least one position ortho to the hydroxyl group unsubstituted. The following molecular structure will illustrate this point. The arrows indicate the unsubstituted positions;

1. Phenol

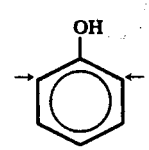

2. Resorcinol

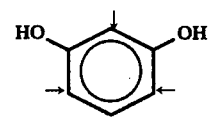

3. Pyrogallol

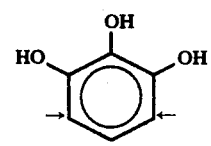

4. Dihydroxydiphenyl Sulfone

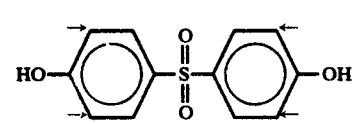

5. p-Napthol

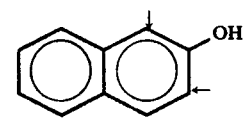

| | | |
|---|---|---|
| 6. p-Cresol | 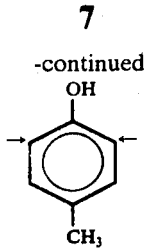 | |
| 7. p-Phenylphenol |  | |
| 8. o-tert-Butylphenol | 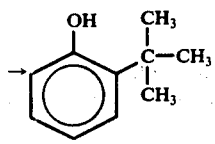 | |
| 9. m-Methoxyphenol | 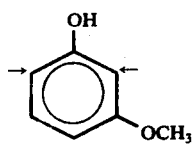 | |
| 10. 3,5-Xylenol | 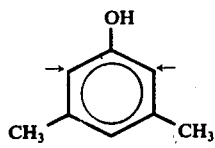 | |
| 11. o-Cresol | 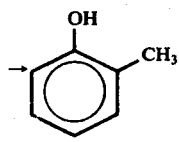 | |
| 12. o-Chlorophenol | 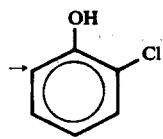 | |
| 13. o-Phenylphenol | 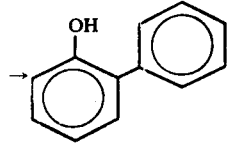 | |
| 14. 2,4-Dichlorophenol | 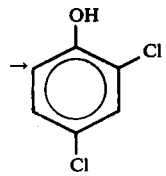 | |

The herein described embodiments and examples of the present invention are not intended to limit its scope; it is to be understood that modifications and variations may be resorted to without departing from the spirit and scope of the invention as claimed herein below.

We claim:

1. A method for preparing a complex of a phenolic compound selected from the group consisting of phenol, resorcinol, dihydroydiphenyl sulfone, B-naphthol, p-cresol, p-phenylphenol, m-methoxyphenol, 3,5-xylenol, o-cresol, o-chlorophenol, o-phenylphenol and 2,4-dichlorophenol comprising: mixing the phenolic compound and hexamethylenetetramine and a suitable solvent in which mixture the amount of solvent is insufficient to dissolve all of the hexamethylenetetramine and all of the phenolic compound simultaneously, and drying the mixture at a temperature less than that which would cause decomposition of the complex.

2. The method of claim 1 wherein the amount of solvent is less than about 30% by weight of the mixture.

3. The method of claim 1 wherein the solvent is water.

4. The method of claim 1 wherein the solvent is nonaqueous.

5. The method of claim 1 wherein the solvent is isopropyl alcohol.

6. The method of claim 1 wherein the solvent is methyl ethyl ketone.

UNITED STATES PATENT OFFICE
CERTIFICATE OF CORRECTION

PATENT NO. : 4,069,220
DATED : January 17, 1978
INVENTOR(S) : Henry Philip Orem et al.

It is certified that error appears in the above–identified patent and that said Letters Patent are hereby corrected as shown below:

Column 6, line 64, "p-Napthol" should be --B-Napthol--.

Signed and Sealed this

Ninth Day of January 1979

[SEAL]

Attest:

RUTH C. MASON
Attesting Officer

DONALD W. BANNER
Commissioner of Patents and Trademarks